United States Patent [19]

Vassiliadis et al.

[11] 4,412,543

[45] Nov. 1, 1983

[54] APPARATUS FOR DETERMINING THE CONCENTRATION OF A FLUORESCENT MATERIAL IN AN EYE

[75] Inventors: Arthur Vassiliadis, Palo Alto; Michael H. Brewer, Felton; Robert E. Myers, Menlo Park, all of Calif.

[73] Assignee: Xanar, Inc., Colorado Springs, Colo.

[21] Appl. No.: 248,881

[22] Filed: Apr. 9, 1981

[51] Int. Cl.³ .............................................. A61B 5/00
[52] U.S. Cl. .................................... 128/633; 128/665
[58] Field of Search ................................ 128/645-649, 128/745, 303 R, 303.1, 633-634, 664-665; 356/152-153, 337-338, 340, 343; 351/6, 9, 14, 213; 73/DIG. 11; 372/23

[56] References Cited

U.S. PATENT DOCUMENTS

| | | | |
|---|---|---|---|
| 3,585,849 | 6/1971 | Grolman | 128/648 |
| 3,756,073 | 9/1973 | Lavallee et al. | 128/648 |
| 3,832,890 | 9/1974 | Grolman et al. | 128/648 |
| 3,963,019 | 6/1976 | Quandt | 128/633 |
| 4,003,707 | 1/1977 | Lubbers et al. | 128/634 X |
| 4,178,917 | 12/1979 | Shapiro | 128/633 X |
| 4,251,139 | 2/1981 | Matsumura | 351/6 X |
| 4,305,398 | 12/1981 | Sawa | 128/745 X |

FOREIGN PATENT DOCUMENTS 2737233 3/1979 Fed. Rep. of Germany .... 73/DIG. 11

519188 8/1976 U.S.S.R. ............................ 128/665

OTHER PUBLICATIONS

EG and G Reticon S-Series Solid State Line Scanners 128, 512, and 1024 Elements.
Cunha-Vaz et al., Early Breakdown of the Blood-Retinal Barrier In Diabetes, British J. Ophthal., 1975, pp. 649-656.
Krupin et al., Vitreous Fluorophotometry in Juvenile-Onset Diabetes Mellitus, Arch Ophthalmol.-vol. 96, May, 1978, pp. 812-814.
Krupin et al., Vitreous Fluorophotometry in Diabetes Mellitus, American Academy of Ophthal., Oct., 1978, pp. 137-141.

Primary Examiner—Lee S. Cohen
Assistant Examiner—Angela D. Sykes
Attorney, Agent, or Firm—Michael A. Kaufman

[57] ABSTRACT

A fluorophotometer for determining the concentration of a fluorescent material in an eye, including a light source producing a beam of light traversing a path in the eye to excite the material to emit fluorescence, optics for imaging the path and fluorescence at a detecting plane, a linear photodiode array at the detecting plane for detecting the fluorescence along the path, and a microprocessor for collecting data from the array and producing information of the concentration of the fluorescent material.

6 Claims, 9 Drawing Figures

FIG_1

FIG_2

FIG_6

FIG_8

APPARATUS FOR DETERMINING THE CONCENTRATION OF A FLUORESCENT MATERIAL IN AN EYE

DESCRIPTION

1. Technical Field

This invention relates to apparatus for determining the concentration of a fluorescent material in an eye and, more particularly, to a fluorophotometer for measuring the concentration of fluorescein in the eye.

2. Background Art

Fluorophotometry is a technique used in ophthalmology for the study of physiological and pathological conditions of the eye. For example, fluorophotometry has been proven useful in research and clinical areas for the evaluation of retinal diseases or for the early detection of diabetic retinopathy. Fluorophotometry employs a fluorescent material, such as fluorescein, which is administered intravenously into a patient. It has been found that in a healthy eye, ocular barriers prevent the passage of fluorescein through the retinal vessels into the vitreous. In a diseased eye, a breakdown occurs of the ocular barriers, resulting in the leakage into, or concentration of, the fluorescein in the vitreous. A direct correlation has been shown between the fluorescein concentration in the vitreous and the degree of retinopathy in the diabetic.

Many other uses have been found for fluorescein in ophthalmology. Although any fluorescent material could be used, fluorescein has been used because of its very low toxicity and effective fluorescence. Thus, fluorophotometry has been used in tear flow studies, corneal permeability studies, aqueous flow studies, lens permeability measurements, and more recently in the vitreous studies. In all these applications, a sensitive fluorophotometer is necessary in order to measure fluorescein concentration at various parts of the eye.

Accordingly, objective fluorophotometers have been developed to determine or measure quantitatively the concentration of fluorescein in, for example, the vitreous. One type of fluorophotometer includes a slit lamp that produces a slit beam of light which is filtered to pass only wavelengths that excite the fluoroescein in the eye. The slit beam is propagated along a path in the eye and is focussed on a target, for example, on the retina. Any fluorescein along the path will absorb at least a portion of the beam to produce fluorescence, while the portion of the beam not absorbed will be scattered or transmitted.

A photometric detecting system of the fluorophotometer has a fibreoptic probe that is moved so as to be superimposed at any position on one point or area of the image of the path traversed by the beam to receive the fluorescence and light scattering. A photomultipler receives the output of the fibreoptic probe and is connected to a photometer which, thus, measures the intensity of the fluorescence. A barrier filter also is used in the photometric detection system to pass the fluorescence to the photomultiplier and substantially attenuate the light scattering. The measurements can be read out in hard copy on a recorder or stored as soft copy in an oscilloscope having storage.

One disadvantage of the prior objective fluorophotometer is that a measurement of only a single point in the eye could be made at one time. In order to obtain additional readings in the eye, the instrument, and in particular, the fibreoptic probe, has to be moved to a new position and another reading taken. In addition to the disadvantage of requiring movable optics to take readings, this has the inherent problem of not providing an accurate measurement of the location of the reading.

Another disadvantage relates to the use of the photomultiplier as part of the photometric detection system. Although the photomultiplier is a sensitive detector, calibration of the detection system using the photomultiplier is difficult to maintain and frequent calibration checks are required.

Yet another disadvantage of the prior fluorophotometer is that the fibreoptic probe of the photometric detection system is positioned in the ocular used by the operator to view the patient's eye. Thus, reflections of light from the operator's eye could affect the photodetection system and influence the fluorescein measurements.

Still furthermore, the prior fluorophotometer does not embody state of the art electronic circuitry that can provide accurate calculations very quickly and present data in useful form for the operator or physician.

SUMMARY OF THE INVENTION

It is an object of the present invention to provide a novel apparatus for determining physiological and pathological conditions in the eye.

It is another object of the present invention to provide such an apparatus using nonmovable optics and the simultaneous reading of a plurality of points in the eye having fluorescence.

Yet another object of the present invention is to provide such an apparatus which is not sensitive to reflections of an operator's eye and which does not require frequent calibration.

Still a further object of the present invention is to provide such an apparatus embodying state of the art technology.

These and other objects of the present invention are obtained through the use of an apparatus for determining the concentration of a fluorescent material in an eye, the fluorescent material being excited with an excitation beam of light entering and traversing a path in the eye to produce fluorescence along the path, comprising means for imaging the path to provide the fluorescence at a detecting plane, means for detecting at the detecting plane the fluorescence along the path and for generating signals representing the detected fluorescence, and means for generating information identifying the concentration of the fluorescent material along the path in response to the signals.

With the entire path traversed in the eye by the excitation beam being imaged at the detecting plane, the means for detecting can simultaneously detect substantially all the fluorescence without moving any components. The information generating means can then collect data of the fluorescence detected by the detecting means and make calculations to produce a measurement of the concentration of the fluorescent material along the path. The detecting means can include a linear photodiode array and the information generating means can embody microprocessor-based technology.

DETAILED DESCRIPTION OF THE INVENTION

Figure 1:
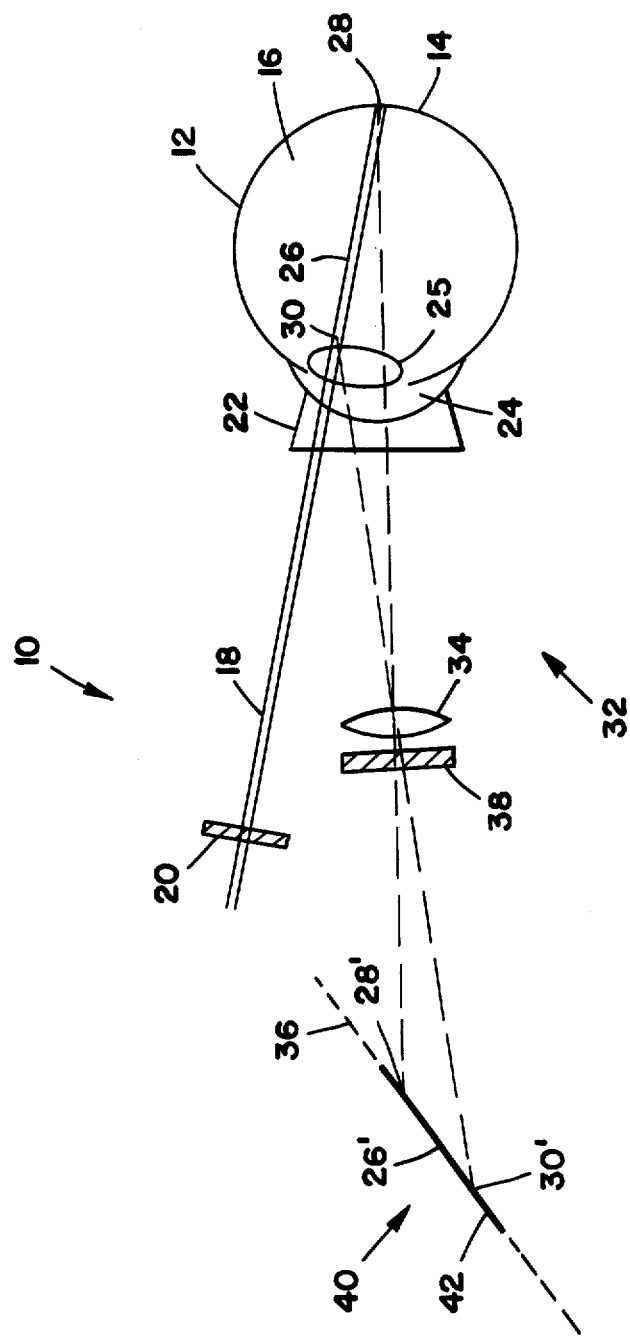
FIG. 1 is a schematic illustration of the optics of the present invention.

FIG. 1 shows a simple optical system 10 that embodies the principles of the present invention and is used to study the physiological or pathological conditions of an eye 12. It is assumed that a patient has been injected intravenously with, or otherwise has received, a fluorescent material (not shown), such as fluorescein, which is now present in the eye 12. As is well-known, if the patient has a healthy eye 12, there is an ocular barrier that prevents the passage of fluorescein through the vessels of, for example, the retina 14 into the vitreous 16. However, if the patient has, for example, a retinal disease, or is a diabetic, a breakdown of the ocular barrier occurs and the fluorescein will leak into and accumulate in the vitreous 16. While the present invention will be described primarily in connection with vitreous studies, its use in the other applications previously described, such as corneal permeability studies, will become apparent.

FIG. 1 shows an excitation beam of light 18 that has been filtered by a filter 20 which passes only wavelengths that can excite fluorescein. This excitation beam of light 18 is transmitted into the eye 12 through a corneal contact lens 22 that has been placed on the eye 12 to cancel the refraction of the cornea 24. The excitation beam of light 18 can be a slit beam, as will be further described.

The excitation beam of light 18 entering the eye 12 propagates through the eye lens 25 and along a path 26 in the vitreous 16, and is focussed on a target, i.e., the retina 14 in this example. Any fluorescein that has accumulated in the vitreous 16 along the path 26 between an end point 28 and an end point 30 of the path 26 will absorb a portion of the light 18 and, thereby, produce fluorescence. The other portion of the light 18 that is not absorbed will be scattered by the vitreous 16. The distinction between the fluorescence and the light scattering is that the range of wavelengths of the fluorescence is different than the wavelength of the light scattering, the latter being the same as the excitation beam of light 18.

A data gathering optics shown generally at 32 has a lens 34 which forms an image 26' of the path 26 at a detecting plane 36. The image 26' has the corresponding end point 28' and end point 30'. A barrier filter 38 functions to pass the fluorescence and substantially attenuate the light scattering. Consequently, an image of any fluorescence along the path 26 is produced at the detecting plane 36. As may be appreciated from FIG. 1, in order to obtain optical data of the fluorescence occuring along the path 26, the data gathering optics 32 should be offset angularly from the excitation beam of light 18. For example, an angle of 20° may be used in order to obtain data from the retina 14 at point 28 and anteriorly to the lens 25 at point 30.

A stationary detector 40 is positioned at the locus of the image 26' to detect simultaneously any and all of the fluorescence produced along the path 26. Preferably, the detector 40 includes a solid-state, linear photodiode array 42 having a plurality of individual detector elements, as will be further described. The linear photodiode array 42 is at an angle such that the entire path 26 is imaged or simultaneously in focus at the various detector elements of the array 42. Thus, without any motion of the data gathering optics 32, detection of the fluorescein can be made along the whole path 26 imaged on array 42 as path 26'. As will be described below, data is obtained from the individual detector elements by electronically scanning the array 42.

Figure 2:
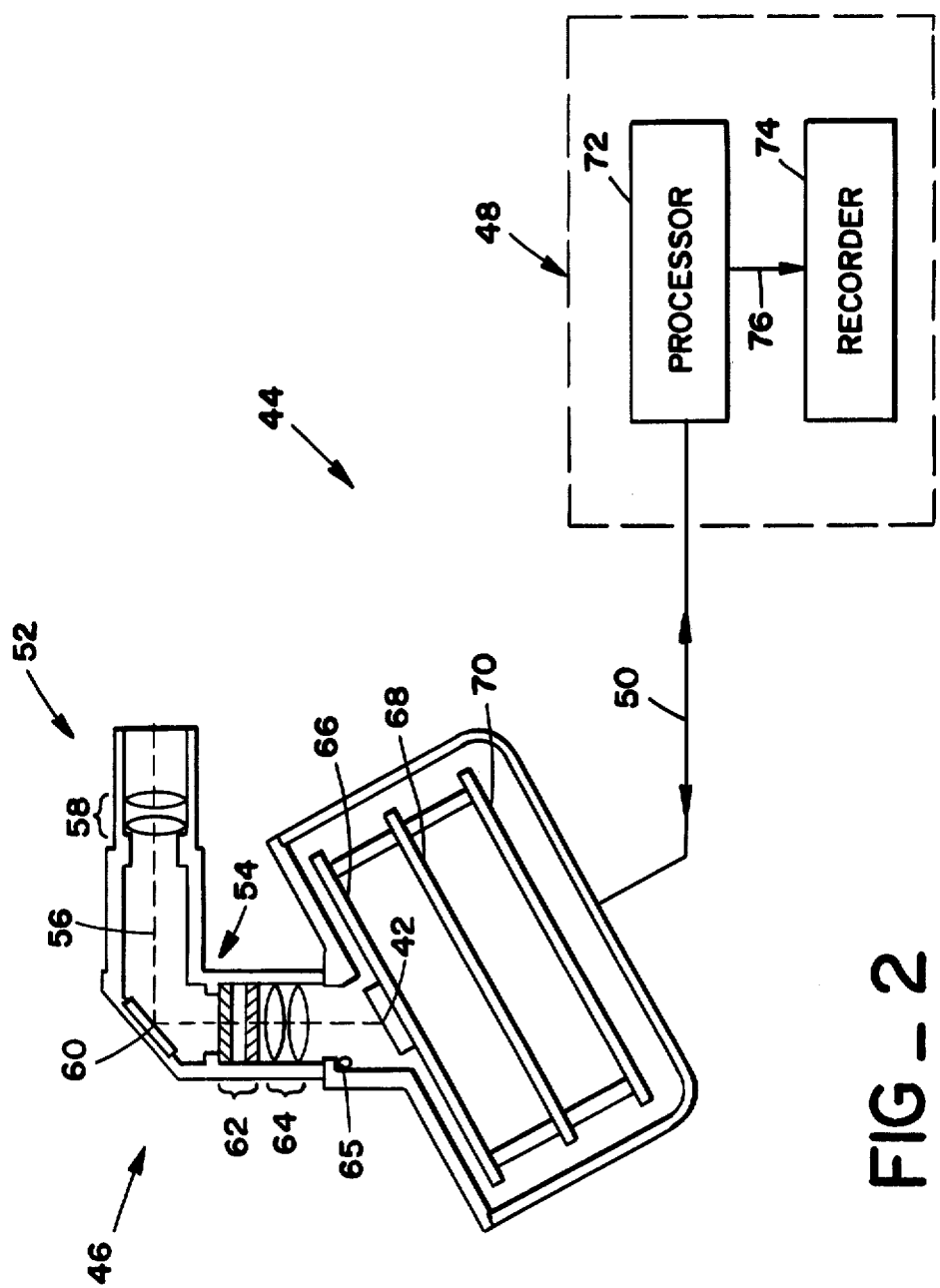
FIG. 2 shows, schematically, one practical embodiment of the present invention.

FIG. 2 illustrates one embodiment of a practical apparatus 44 of the present invention that can be used in combination with any well-known "slit-lamp" (not shown), such as a Haig-Streit slit-lamp. A "slit-lamp" is an instrument that generates a beam of light that is made into a thin slit of light similar to the beam of light 18. The filter 20 would be added to the "slit-lamp" to produce the previously described excitation wavelengths. The "slit-lamp" also has a binocular microscope, with one eyepiece being used by the operator to view the various parts of the eye 12 and the other eyepiece being replaced by the apparatus 44, as will now be described.

The apparatus 44 includes a self-contained head 46 and a separate console 48 coupled together over an electrical communication line 50. The head 46 has a tubular housing 52 that can be installed on the "slit-lamp" in place of the other eyepiece to receive any of the fluorescence being produced along the path 26 of the eye 12. An optics 54 supported in the tubular housing 52 includes, along an optical axis 56, a pair of lenses 58, a mirror 60 which serves to fold the optical axis 56 into a practical configuration, a pair of barrier filters 62 which perform the same function as barrier filter 38, and a pair of lenses 64. Head 46 also supports a reference light emitting diode (LED) 65 for purposes to be described.

Lenses 58 and lenses 64 form an image of the path 26 onto the linear photodiode array 42 which is contained on a detector printed circuit (PC) board 66. The self-contained head 46 also includes an analog-to-digital (A/D) PC board 68 and an electronic timing or clock PC board 70.

The console 48, as will be further described, includes a data processor 72 which communicates with PC board 66, PC board 68, and PC board 70. Data processor 72 collects data and calculates or measures the concentration and/or distribution of fluorescein along a plurality of points of the path 26. The measurements and/or distribution are provided in hard copy form on a recorder 74 coupled to data processor 72 over a line 76.

Figure 3:
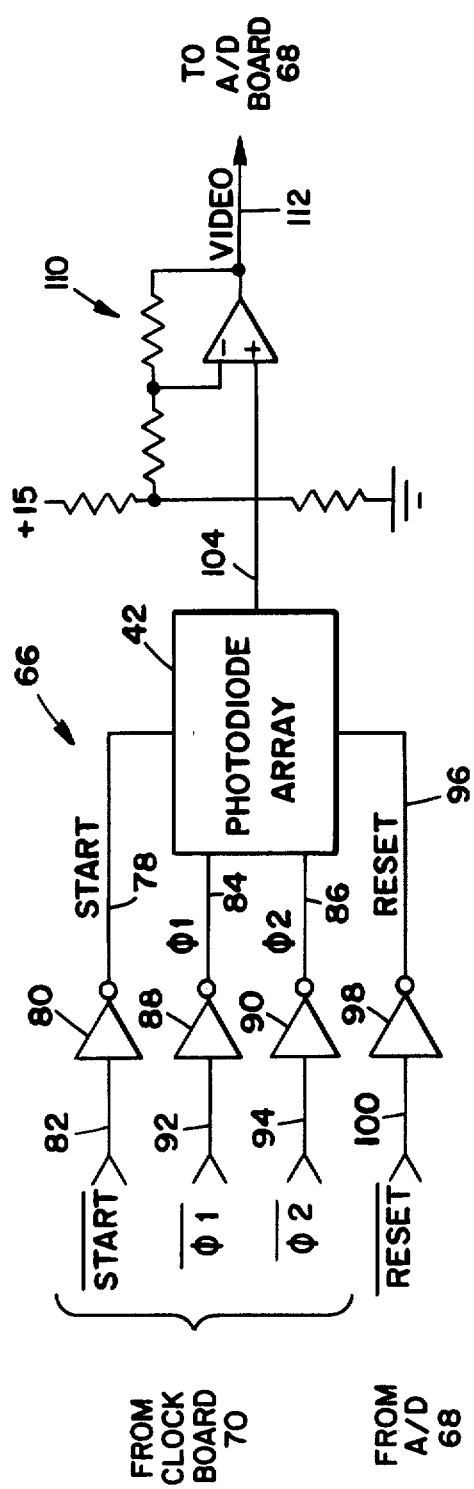
FIG. 3 illustrates, schematically, a detector printed circuit board of the present invention.

As previously indicated, one example of detector 40 can be linear photodiode array 42, which array can be model Reticon S-Series Solid State Line Scanner 128, manufactured by EG+G Reticon, Sunnyvale, California. As shown in FIG. 3, the linear photodiode array 42 on the PC board 66 receives periodic pulses START on a line 78, via an inverter 80 which inputs periodic pulses START on a line 82, to initiate a scan of array 42. Array 42 also receives a pair of out-of-phase clock pulses $\phi_1$ and $\phi_2$ on respective lines 84, 86 via inverters 88, 90, which input clock pulses $\phi_1$, $\phi_2$ on lines 92, 94, to drive array 42 to read out detected data. Array 42 also receives periodic pulses RESET on a line 96 via an inverter 98, which inputs periodic pulses RESET on a line 100, for reset purposes to be described. Pulses START and pulses $\phi_1$, $\phi_2$ are produced on the clock PC board 70, whereas pulses RESET are produced on the analog-to-digital PC board 68.

Figure 4:
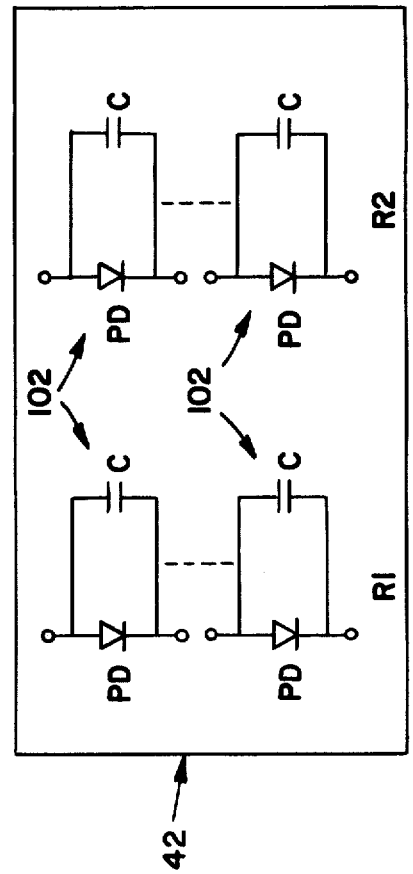
FIG. 4 is a simplified block diagram of a linear photodiode array of the present invention.

The linear photodiode array is shown in more detail in FIG. 4, though reference may be made to the above-mentioned Reticon S-Series for still further details. Array 42 may contain a plurality of detector elements shown generally at 102. Each one of the detector elements 102 includes a photodiode PD, being activated in response to the fluorescence at a corresponding point on the path 26, and an associated storage capacitor C. For example there may be a total of 128 detector elements 102 arranged in two rows $R_1$ and $R_2$, with each row aligned side-by-side along the image 26' of path 26 and sharing a common output 104. This creates, in effect, an array 42 with sixty-four detector elements 102 with increased photosensitive area.

In the operation of scanning the linear photodiode array 42, the time between two consecutive pulses START is called an integration period. During this period, when the fluorescence is being imaged onto, and activating, the photodiodes PD, a charge previously stored on each capacitor C is gradually removed due to the flow of a reverse current through an associated photodiode PD. This reverse current includes a photocurrent that is proportional to the fluorescence, and a dark current that results from, or may be treated as, background level. The amount of charge that will be replaced on each capacitor C during a scanning of the array 42 is a product of the reverse current and the integration period.

Then, when a pulse START occurs, a scan of the array 42 begins and the detector elements 102 are individually clocked by pulses $\phi_1$, and pulses $\phi_2$. During this sequencing, the charge is replaced on each capacitor C. Consequently, a train of sixty-four analog pulse signals is produced on output 104 of array 42 for each scan, each analog pulse signal being proportional to the charge replaced on an associated capacitor C and, hence, to the intensity of the fluorescence and the background level acting on the associated photodiode PD.

With reference again to FIG. 3, an operational amplifier shown generally at 110 amplifies each of the sixty-four analog pulse signals on output 104 to produce corresponding amplified analog pulse signals on an output line 112. These signals on line 112 are fed to the analog-to-digital PC board 68.

Figure 5:
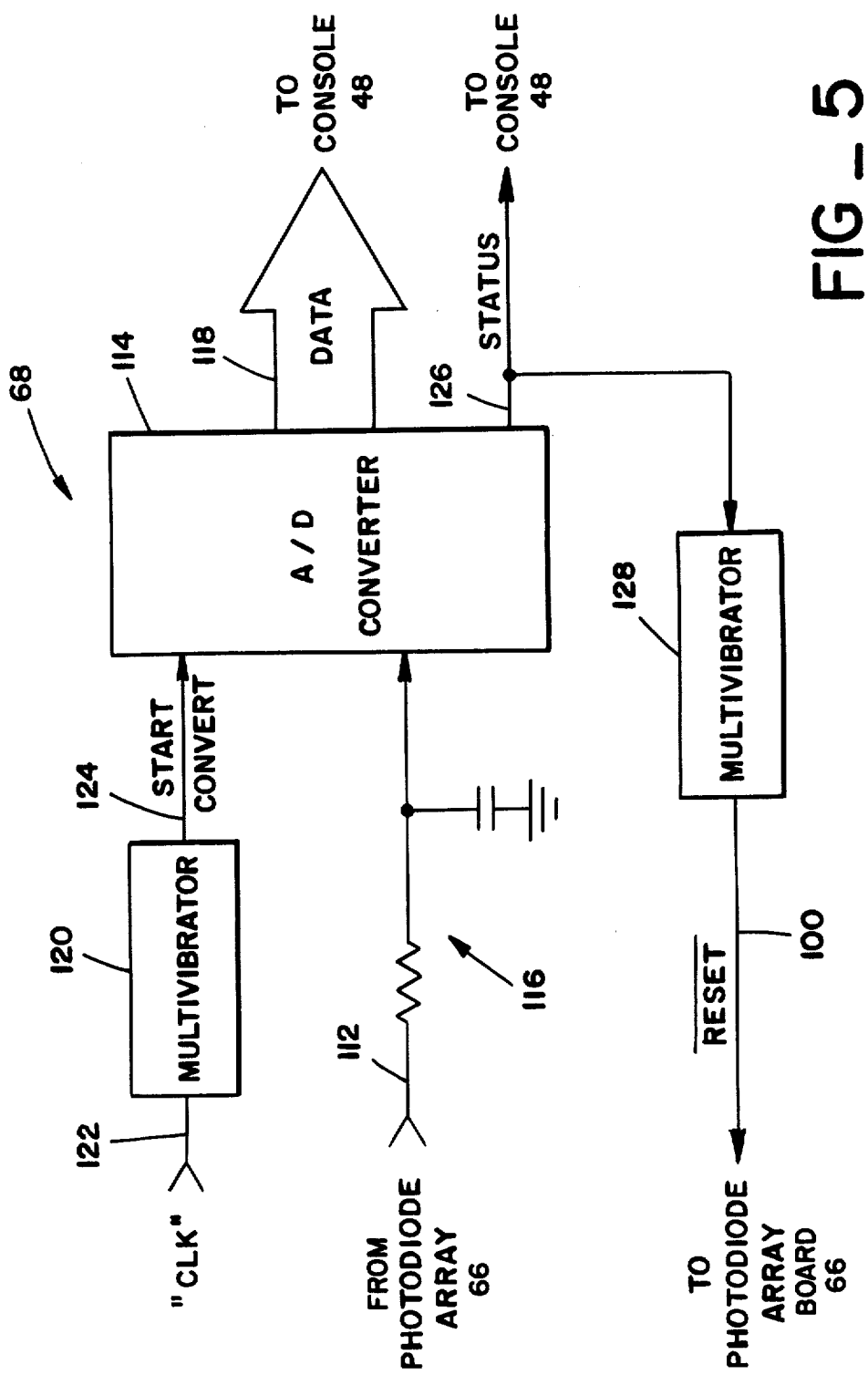
FIG. 5 shows, schematically, an analog-to-digital printed circuit board of the present invention.

FIG. 5 shows an analog-to-digital (A/D) converter 114 that is part of the PC board 68. Converter 114 receives the train of the analog pulse signals on line 112 for each scan through an RC filter 116, converts each of these analog pulse signals to respective digital signals or data words of, for example, 12-bit length, and outputs the data words on a data line 118. A one-shot multivibrator 120 is triggered by clock pulses on a line 122 to produce, via a line 124, pulses START CONVERT for each of the signals on line 122 to start the conversion. At the end of the conversion of each of the signals on line 112, converter 114 generates a pulse STATUS on a line 126 which identifies that a data word is available from the converter 114. The pulse STATUS also triggers a one-shot multivibrator 128 which then produces the pulse RESET on the line 100 that is coupled to inverter 98 ultimately to reset a corresponding capacitor C of a detector element 102. This reset fully charges such a capacitor C in anticipation of another scan.

In the overall operation of PC board 68, each clock pulse arriving on line 122 triggers multivibrator 120 which produces the pulse START CONVERT about 325 microseconds later. This delay is related to the start of the clocking of each detector element 102 and ensures that the conversion process of each signal on line 112 is initiated well into the clocking or output of such a detector element 102. This delay is used since the RC filter 116 causes the leading edge of a signal inputted to converter 114 to be sloped. Thus, the delay allows the conversion to occur when the level of each signal into converter 114 has reached a flat level. The converter 114 completes the conversion of each signal in about 65 microseconds, and then produces the signal STATUS on line 126.

Figure 6:
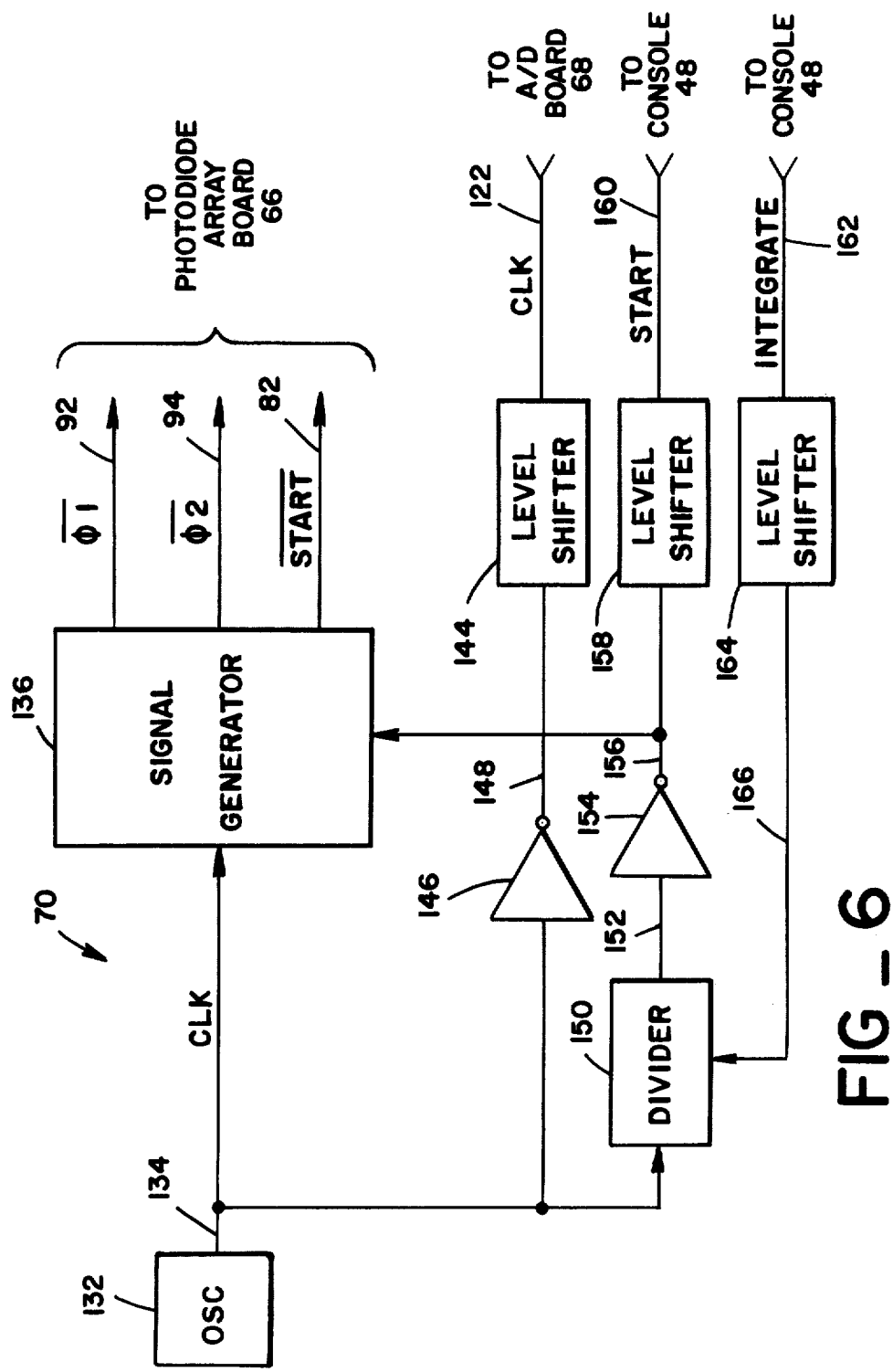
FIG. 6 is a schematic illustration of a timing printed circuit board of the present invention.

With reference to FIG. 6, the timing or clock PC board 70 includes an astable multivibrator 132 which is free running and produces a clock pulse frequency signal on a line 134. A signal generator 136 is driven by the frequency signal on line 134 to produce the pulse START on line 82 that is fed to inverter 80 of PC board 66, as well as the pulse $\phi_1$ and pulse $\phi_2$ on line 92 and line 94 coupled to the input of inverter 88 and inverter 90, respectively. Signal generator 136 includes two flip-flops (not shown) which are wired so that pulse $\phi_1$ and pulse $\phi_2$ are out of phase relative to each other for the proper operation of linear photodiode array 42.

A level shifter 144 is driven by the frequency signal on line 134 via an inverter 146 and a line 148 to level shift the frequency signal and produce the pulses on line 122 that trigger the multivibrator 120 of PC board 68.

A divider 150 divides the frequency signal on line 134 to produce periodically a pulse on a line 152. An inverter 154 is driven by the pulse on line 152 to produce a pulse on a line 156 that activates signal generator 136 to produce the pulse START at this time. A level shifter 158 is coupled to line 156 to also produce at this time, on a line 160, a level shifted pulse START which informs data processor 72 of the start of a scan and, therefore, that sixty-four, 12-bit data words soon will be available for processing.

Divider 150, for example, divides the frequency signal on line 134 by 384, thus generating a pulse START every predetermined period. This division factor may be changed by data processor 72 generating a pulse INTEGRATE on a line 162, which is shifted by a level shifter 164 to control divider 150 via a line 166. For example, if the intensity of the fluorescence is low, causing the capacitors C to discharge slowly, then the above-mentioned division factor of 384 is employed to provide, in effect, a relatively long integration period. If the intensity of the fluorescence is high, causing the capacitors C to discharge quickly, the division factor can be made, for example, to be 128, resulting in the pulse START being generated over a shorter period, i.e., producing a shorter integration period.

Figure 7:
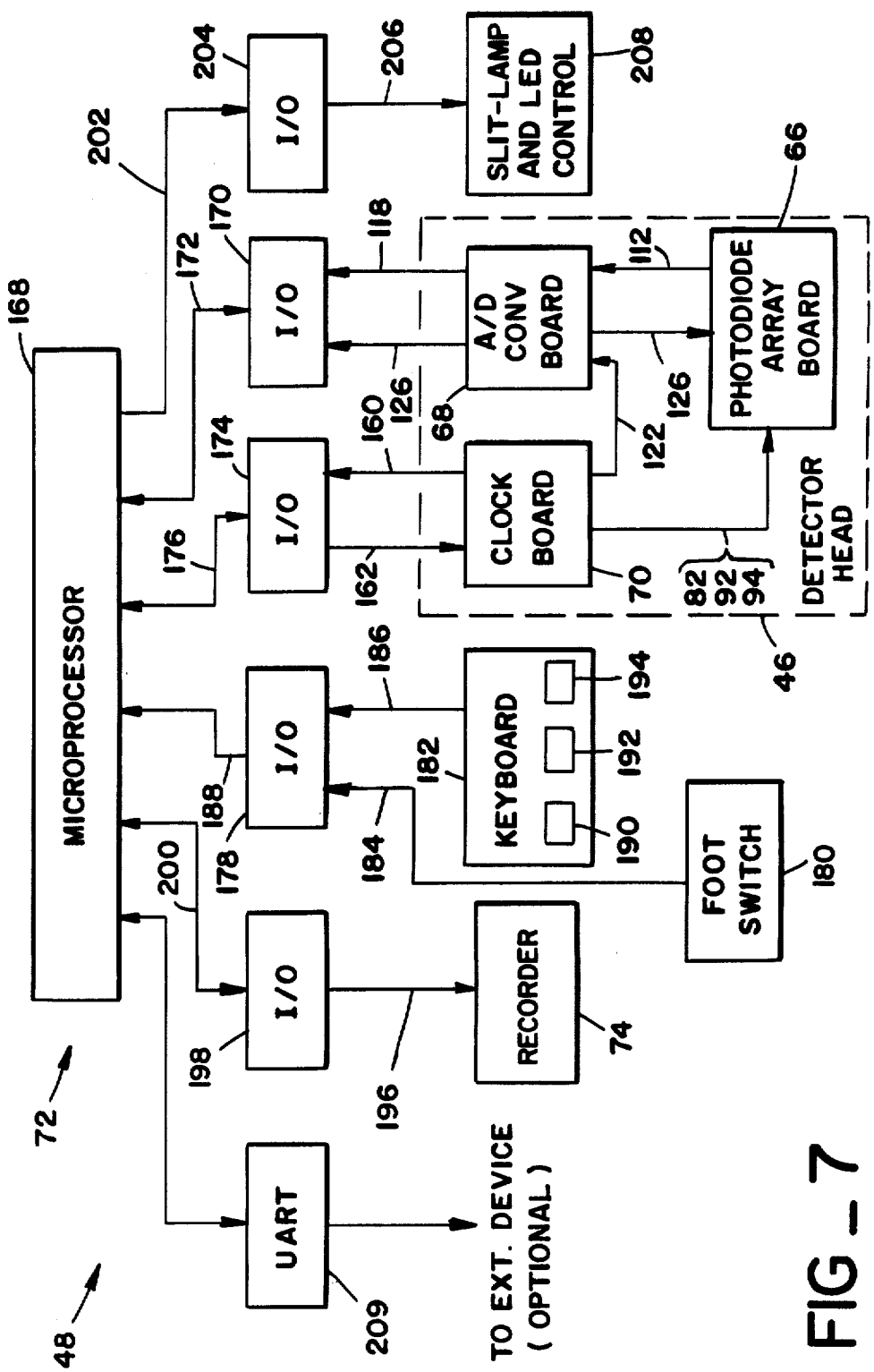
FIG. 7 is a block diagram of a data processor of the present invention.

FIG. 7 illustrates in more detail the console 48 in combination with PC boards 66, 68, 70 of the head 46. The data processor 72 can include, for example, a microprocessor 168, such as model 8085 A manufactured by the Intel Corporation, Santa Clara, Calif. While not shown, the microprocessor 168 is on a board that also has an address decoding circuit, 6 kilobytes of read only memory (ROM), 6 input/output (I/O) ports, and an RS-232 serial port. Microprocessor 168 receives a series of sixty-four 12-bit data words from PC board 68 for each scan through an I/O device 170 coupled between line 118 and a line 172. The start of each such series of data words is indicated by the pulse START on line 160 which is received by microprocessor 168 via an I/O device 174 and a line 176. The availability of each data word in the series is indicated by the pulse STATUS on line 126 that is coupled through I/O device 170 and line 172 to microprocessor 168. Microprocessor 168 also communicates with the PC board 70 through line 176, I/O device 174 and line 162 to control the division factor of divider 150 and, hence, integration period of array 42.

An I/O device 178 communicates a foot switch 180 and a keyboard 182 with microprocessor 168 via a line 184 and a line 186, respectively, and via a line 188. The foot switch 180, when depressed, generates a command for initiating a main program to be described below for obtaining the data from head 46 on the fluorescein concentration in the eye 12. Keyboard 182 has a RESET key 190 which, when depressed, resets microprocessor 168, discontinuing whatever operation is in progress, and executing the main program from the beginning. Keyboard 182 also has a CAL key 192 which, when depressed, causes microprocessor 168 to branch to a subroutine which executes the calibration of the head 46, as will be further described. Another COPY key 194 on keyboard 182, when depressed, causes microprocessor 168 to branch to a subroutine that prints an extra copy of a data printout, but utilizing a different graph scale than an original printout.

Data are displayed on the recorder 74, such as a thermal printer, which communicates with microprocessor 168 through a line 196, an I/O device 198 and a line 200. Microprocessor 168 also controls the turning on and off of the slit-lamp (not shown) and the reference LED 65 via a line 202, an I/O device 204, a line 206, and a control 208. Microprocessor 168 can also output the data to an optional external device via its RS-232 serial port and a UART 209.

In the overall operation of the apparatus 44, assume that the head 46 is mounted on a slit-lamp (not shown) in place of one of the eyepieces so as to receive the fluorescence, and that the apparatus 44 has been calibrated, as will be further described. When the power is then turned on, microprocessor 168 performs an initialization procedure or program. This includes turning on the light source of the slit-lamp to produce the beam of light 18, turning off the reference LED 65, activating the foot-switch 180 and keyboard 182, and controlling the thermal printer 74 to print the message READY.

The slit-lamp is then manipulated to have the beam of light 18 enter the eye 12 and be focussed on the target of interest. For example, for a scan of the vitreous 16, the beam of light 18 would be focussed on the retina 14, as shown in FIG. 1, whereas for a scan of anterior parts of the eye 12, the beam of light 18 would be focussed on the posterior portion of the lens 25. Consequently, under the assumption that the beam of light 18 is focussed on the retina 16, the path 26, and fluorescence along the path 26, are imaged on the linear photodiode array 42.

Then, the foot-switch 180 is depressed, thereby starting the main program. Under program control, microprocessor 168 collects data from A/D PC board 68 for a plurality of scans of linear photodiode array 42, for example fifteen scans, each time storing sixty four 12-bit numbers from each scan. Thereafter, the light source producing the beam of light 18 is switched off by microprocessor 168 via I/O device 204 and control 208. After a short delay, data from another fifteen scans of the linear photodiode array 42 are collected in the dark and stored to obtain values for the dark current. Next, after a short delay, the reference LED 65 is turned on and yet another fifteen scans of the array 42 are made to collect and store data for calibration purposes.

Microprocessor 168, under program control, then uses all of the collected data from the total of forty-five scans. The dark current data obtained with the second of the fifteen scans is subtracted from the data obtained with the first fifteen scans. The results are then corrected for calibration purposes by using the data obtained with the last of the fifteen scans. The reference LED 65 then is turned off and the light source in the slit-lamp is turned on in readiness to perform another such procedure. Also, output data is then printed on the thermal printer 74.

Before describing the alternative embodiment of FIG. 8, a description of the operation and general content of the computer program listings for determining the fluorescein concentration will now be given. The computer program listings are at the end of this description and before the claims. The title, operation and general content of the listings are as follows:

1. MAIN.MAC—This is the main control program that runs continuously, scanning the foot-switch 180 and keyboard 182 to perform designated routines. This main control program performs its routine on power-up.
2. BLOCK.MAC—This routine prepares and transmits to the printer 74 blocks of numbers that represent the data output.
3. PLOT.MAC—This routine is the main subroutine for formatting and sending calculated output data to thermal printer 74.
4. LITE.MAX—This routine controls the intensity of the beam of light 18, the intensity of the reference LED 65, and the length of the integration period.
5. REQ.MAC—This routine detects the START signal from the PC board 70 preceeding a scan of linear photodiode array 42.
6. GET.MAC—This routine monitors the STATUS signal from the A/D converter 114 and governs the receipt of data words by the microprocessor 168.
7. METFLN.FOR—This Fortran routine is the main routine for gathering and manipulating the data from A/D PC board 68 and for preparing calibration data.

Figure 8:
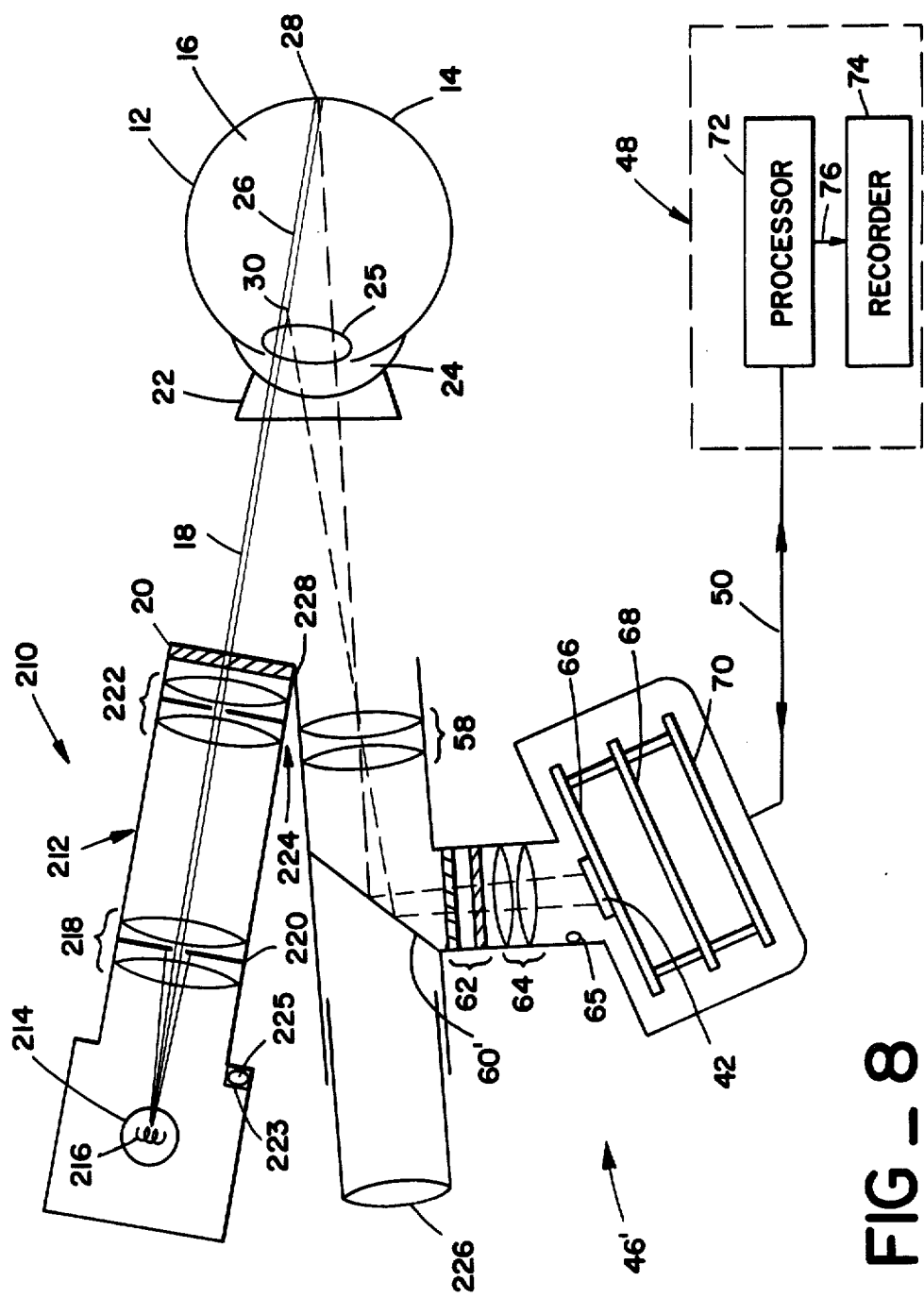
FIG. 8 illustrates, schematically, another practical embodiment of the present invention.

FIG. 8 illustrates an alternative embodiment or apparatus 210 for determining the concentration of a fluorescent material, such as fluorescein, in the eye 12. FIG. 8 and FIG. 2 show like reference numerals to indicate like elements. Essentially, the difference between apparatus 210 of FIG. 8 and apparatus 44 of FIG. 2 is that the former contains a light source 212 for producing the beam of light 18.

Source 212 includes an incandescent lamp 214 having a compact filament 216. A pair of lenses 218 and a slit 220, together with a pair of lenses 222 and a slit 224, form the slit beam of light 18 that is filtered by filter 20. A filter 223, which is the same as filter 20 to pass only the excitation wavelength, and a light detector 225, are used to sense the intensity of the excitation beam of lamp 214. Under control of microprocessor 168, which receives data from detector 225, the lamp intensity can be adjusted to appropriate levels should it deteriorate after much usage and time.

Apparatus 210 also includes a head 46' that is similar to head 46. The head 46' uses a dichroic beam splitter 60' in place of mirror 60 and, in addition, an eyepiece 226. The dichroic beam splitter 60' transmits the light scattering through the eyepiece 226, but reflects the fluorescence to the linear photodiode array 42. Source 212 and head 46' are coupled together at 228 to provide the appropriate angular spacing between the beam of light 18 and the data gathering optics in head 46', as mentioned for FIG. 1. As may be appreciated, an operator may look through eyepiece 226 to adjust the apparatus 210 to focus the beam of light 18 on, for example, the retina 14 for vitreous fluorophotometry, and to otherwise properly aim and orient the apparatus 210. The use of the beam splitter 60' also serves to eliminate or at least minimize any reflections from the operator's eye when viewing through the eyepiece 226.

Apparatus 210 also includes the console 48. The use and operation of apparatus 210, including the functions performed with the previously described computer program listings, are the same as described for apparatus 44.

Figure 9:
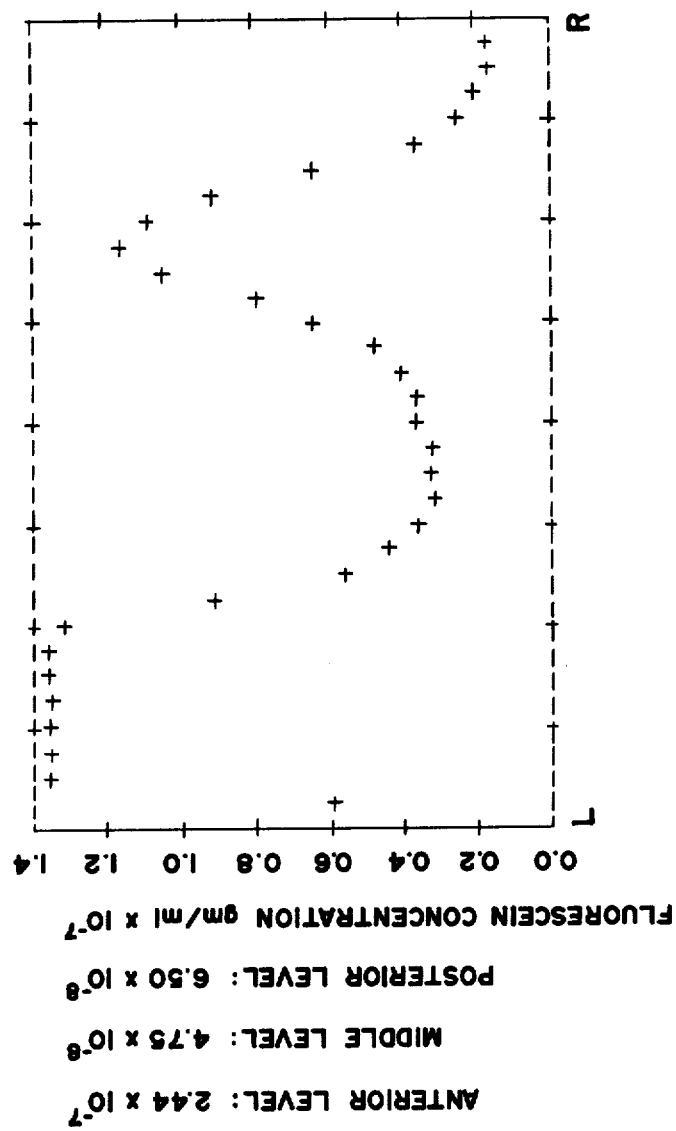
FIG. 9 is a diagram showing an example of the measurements obtained with the present invention.

FIG. 9 illustrates examples of the read-out of fluorescein concentration that are obtained with the present invention. The plot in FIG. 9 shows the fluorescein concentration at thirty-two points along path 26 between point 28 and point 30 from the retina R to the lens L. FIG. 9 also shows a numerical readout of the fluorescein concentration at these thirty-two points.

With reference to the calibration of apparatus 44 or apparatus 210, prior to initial use a cuvette (not shown) having a known concentration of fluorescein, e.g. $10^{-7}$ gm/ml, is placed in front of the slit-lamp where the eye 12 normally would be. The CAL key 192 is then depressed to take a measurement by scanning photodiode array 42 in accordance with the procedure as previously described. If the output data of this scan does not read the known concentration, i.e., $10^{-7}$ gm/ml, then the intensity of reference LED 65 is adjusted with a potentiometer (not shown) and other scans taken until this concentration data is obtained. Microprocessor 168 now stores data which is calibration data of the photodiode array 42 whose output might vary slightly during use due to, for example, temperature changes. Then, when apparatus 44 or apparatus 210 is used to detect the fluorescein concentration in the eye 12, the last of the fifteen scans, in which only reference LED 65 is lit, provides data which is related to the calibration data to make appropriate compensation for reading out the concentration data shown in FIG. 9. This compensation is made for each of the detector elements and for each scan to make highly accurate measurements, though the array 42 is a highly stable device whose output should vary little with temperature. Furthermore, the array 42, being a very stable device, requires infrequent calibration.

In summary, the apparatus of FIG. 1, FIG. 2 and FIG. 8 can obtain data of the fluorescein concentration along the entire path 26 essentially simultaneously and without any movable optics. The linear photodiode array 42 is a very stable device requiring infrequent calibration checks. Furthermore, the array 42 in FIG. 2, or FIG. 8 will not be affected by any light reflections from an operator's eye when viewing the patients's eye 12. Also, the apparatus 44 and the apparatus 210 embody state-of-the-art data processor technology.

Other aspects, objects and advantages of the invention can be obtained from a study of the drawings, the disclosure and the appended claims.

```
;   **************
;   *  MAIN.MAC  *
;   **************
;
;       I/O ROUTINES FOR METRICON MODEL 120 FLUOROPHOTOMETER
;
;       COPYRIGHT (C) FEBRUARY, 1981
;       MIKE BREYER
;       METRICON LTD.
;       1921A OLD MIDDLEFIELD WAY
;       MTN. VIEW, CA., 94043
;
;
;
          ENTRY      MAIN,SERR,SWITCH,AVER,PHEAD,PLOT,HISTYP,SCALE1
          ENTRY      SCALE3,SIGNON,INIT,PLINE,LF,PRFLF,READ,LITEON
          ENTRY      LITEOF,LEDON,LEDOFF,CLOINT,FASINT,BFQ,GET
          EXTRN      FLUPO,XCOPY,XCALIB
          DSEG
STKSPC:   DS         128
STAK      EQU        $
          CSEG
MAIN:     LXI        SP,STAK
          CALL       FLUPO
          JMP        MAIN
SERR:     LXI        H,ERMSG
          CALL       PLINE
          JMP        MAIN
```

```
ERMSG:   DB      'ERROR',0DH,'$'
SWITCH:  IN      20H
         ANI     40H         ;FOOTSWITCH?
         RZ
         IN      20H
         ANI     02H         ;COPY?
         JNZ     XCAL
         CALL    XCOPY
         RET
XCAL:    IN      08H
         ANI     01H         ;CAL?
         JNZ     SWITCH
         CALL    XCALIB
         RET
;
;
;
;
;
;
;
;
;
;
;
;
;
;
;
;
;
;
;
;
;
;
;
;
;
         DSEG
NUMIC:   DS      5
COUNT:   DS      1
NUMIT1:  DS      2
         CSEG
XCAL:    LXI     H,MSGP1
         CALL    PLINE
         LXI     H,MSGP2
         CALL    PLINE
         RET
XCPY:    MVI     C,XX
         CALL    CO
         CALL    CO
         MVI     A,X
         STA     COUNT
         CALL    LOOP
         LXI     H,MSGP1
         CALL    PLINE
         LXI     H,MSGP1
         CALL    PLINE
         RET
LOOP:    SHLD    NUMIT1      ;SAVE POINTER
         MOV     A,M
```

```
            INX     H
            MOV     D,M
            LXI     H,NUMLC
            CALL    BNBCD1
            LXI     H,NUMLC
            MOV     C,M
            CALL    CO
            INX     H
            MOV     C,M
            CALL    CO
            INX     H
            MOV     C,M
            CALL    CO
            INX     H
            MOV     C,M
            CALL    CO
            MVI     C,' '
            CALL    CO
            INX     H
            MOV     C,M
            CALL    CO
            MVI     C,' '
            CALL    CO
            MVI     C,' '
            CALL    CO
            LDA     COUNT
            INR     A
            STA     COUNT
            CPI     32
            RZ
            LHLD    ...
            JPO     ...
            INX     H
            JMP     LOOP
;
; BINARY TO BCD ROUTINE
;
; REGISTER USAGE
; DE    BINARY VALUE
; HL    POINTER TO BCD BUFFER IN MEMORY
; A,F,C USED AS TEMPORARIES
;
BNBCD1:
            LXI     B,10000
            CALL    DIGIT
            LXI     B,1000
            CALL    DIGIT
            LXI     B,100
            CALL    DIGIT
            LXI     B,10
            CALL    DIGIT
            LXI     B,1
            CALL    DIGIT
            RET
MSGE1:  DB      ...
MSGE2:  DB      ...
        DB      ...
;
;
;
;
```

```
;
;
;
;
;
;
;
;
;
;
;
;
;
;
;
;
;
;
;
;
;
;
;
;
;
;
;
;
;
;
;
;
;
;
;
;
;
;
;
;
;          **************
;          *  PLOT.MAC  *
;          **************
;
           CSEG
INIT:      MVI     A,92H      ;PROGRAM PORTS 4,5,6
           OUT     07H
           MVI     A,90H      ;PROGRAM PORTS 8,9,A
           OUT     0BH
           MVI     A,01       ;SET PRNTR STROBE HI
           OUT     0FH
           MVI     A,06H      ;SET LAMP ON, LED OFF, INT LONG
           OUT     06H
           LXI     H,MSG1
           CALL    PLINE
           RET
SIGNON:    LXI     H,MSG2
           CALL    PLINE
           RET
AVER:      MOV     A,M        ;SAVE MESSAGE #
           STA     MSGNO
           XCHG
           SHLD    NUMPT      ;SAVE POINTER TO VALUE
           PUSH    H
           POP     H
           CALL    PUTEXP     ;PRINT EXPONENT
           LDA     MSGNO
           DCR     A
           JZ      LAVMS1
           DCR     A
```

```
            JZ       LEVMS2
            JMP      LEVMS3
LEVMS1:     LXI      H,MSG9
            CALL     PLINE
            JMP      PUTNUM
LEVMS2:     LXI      H,MSGA
            CALL     PLINE
            JMP      PUTNUM
LEVMS3:     LXI      H,MSGB
            CALL     PLINE
            JMP      PUTNUM
PUTNUM:     LHLD     NUMPT
            MOV      E,M
            INX      H
            MOV      D,M
            LXI      H,NUMLOC
            CALL     BINBCD
            LXI      H,NUMLOC
            MOV      C,M
            CALL     CO
            MVI      C,'.'
            CALL     CO
            INX      H
            MOV      C,M
            CALL     CO
            INX      H
            MOV      C,M
            CALL     CO
            LXI      H,MSGC
            CALL     PLINE
            RET
LF:         MVI      C,0DH
            CALL     CO
            RET
PUTEXP:     MOV      A,M          ;SAVE EXP
            PUSH     PSW
            LXI      H,MSG3       ;PRINT SPACES & SIGN
            CALL     PLINE
            POP      PSW
            ADI      30H          ;CONVERT TO ASCII
            MOV      C,A
            CALL     CO           ;PRINT EXP
            MVI      C,0DH
            CALL     CO           ;LINE FEED
            RET
PHEAD:      LXI      H,MSG4       ;PRINT HEADING
            CALL     PLINE
            RET
SCALE1:     LXI      H,MSG5       ;1.4 UNITS FULL SCALE
            CALL     PLINE
            LXI      H,MSG6
            CALL     PLINE
            RET
SCALE3:     LXI      H,MSG8       ;3 UNITS FULL SCALE
            CALL     PLINE
            LXI      H,MSG6
            CALL     PLINE
            RET
PLOT:       SHLD     DPTR
            XRA      A
            PUSH     PSW
```

```
PL0:    POP     PSW
        INR     A
        PUSH    PSW
        CPI     32
        JNZ     PL00
        LXI     H,MSG7
        CALL    PLINE
        POP     PSW
        RET                     ;DONE
PL00:   ANI     3
        JZ      PLUS
        MVI     A,'CH
        STA     FRAME
        CALL    PTPNT
        JMP     PL0
PLUS:   MVI     A,'+'
        STA     FRAME
        CALL    PTPNT
        JMP     PL0
PTPNT:  LHLD    DPTR
        MVI     E,3
        MOV     D,M
        INX     H
        SHLD    DPTR
PT0:    MVI     C,' '
        CALL    CO
        MVI     C,' '
        CALL    CO
        LDA     FRAME
        MOV     C,A
        CALL    CO
PT00:   INR     E
        DCR     D
        JZ      PT01
        MVI     C,' '
        CALL    CO
        JMP     PT00
PT01:   MVI     C,'*'
        CALL    CO
PT1:    MVI     A,34
        CMP     E
        JNZ     PT2
        LDA     FRAME
        MOV     C,A
        CALL    CO
        MVI     C,0DH
        CALL    CO
        RET
PT2:    MVI     C,' '
        CALL    CO
        INR     E
        JMP     PT1
PLINE:  MOV     A,M
        CPI     '$'
        RZ
        MOV     C,A
        CALL    CO
        INX     H
        JMP     PLINE
CO:     IN      08H
        ANI     10H             ;PRNTR BUSY?
```

```
            JNZ     CO
            MOV     A,C
            OUT     0GH         ;DATA TO PRNTR
            XRA     A
            OUT     2BH         ;PRNTR STROBE LO
            INR     A
            OUT     0BH         ;PRNTR STROBE HI
            RET
MSG2:       DB      '   METRICON MODEL 120 FLUORIROTOMETER ',0DH,0DH
            DB      'NAME:                              ',0DH,0DH
            DB      'PATIENT NUMBER:              AGE:      ',0DH,0DH
            DB      'DATE:                        EYE:      ',0DH,0DH
            DB      'DIAGNOSIS :                           ',0DH,0DH,'$'
MSG3:       DB      '                                      ','$'
MSG4:       DB      'FLUORESCEIN CONCENTRATION '
            DB      67H,6DH,'/',6DH,6CH,' X 10',0DH,0DH,'$'
MSG5:       DB      ' 0.0   0.2   0.4   0.6   0.8   1.0   1.2   1.4',0DH,'$'
MSG8:       DB      ' 0.0   0.5   1.0   1.5   2.0   2.5   3.0   3.5',0DH,'$'
MSG6:       DB      'L +----+----+----+----+----+----+----+',0DH,'$'
MSG7:       DB      'R +----+----+----+----+----+----+----+',0DH,'$'
MSG1:       DB      ' READY... ',0DH,0DH,'$'
MSG9:       DB      '        POSTERIOR LEVEL:    ','$'
MSGA:       DB      '        MIDDLE    LEVEL:    ','$'
MSGB:       DB      '        ANTERIOR  LEVEL:    ','$'
MSGC:       DB      ' X 10',0DH,'$'
            DSEG
MSGNO:      DS      1
NUMPT:      DS      2
NUMLOC:     DS      3
FRAME:      DS      1
DITH:       DS      2
            CSEG
;
;
;
; BINARY TO BCD ROUTINE
;
; REGISTER USAGE
; DE - BINARY VALUE
; HL - POINTER TO BCD BUFFER IN MEMORY
; A,B,C - USED AS TEMPORARIES
;
BINBCD:
            LXI     B,100
            CALL    DIGIT
            LXI     B,10
            CALL    DIGIT
            LXI     B,1
            CALL    DIGIT
            RET
;
DIGIT:
            MVI     M,30H       ;INITIALIZE DIGIT
                                ;FOR BCD, DIGIT=0,
                                ;FOR ASCII, DIGIT = 30H
L10:                            ;SUBTRACT LOOP
            MOV     A,E
            SUB     C
            MOV     E,A
            MOV     A,D
            SBB     B
            MOV     D,A
```

```
        JM      DI1
        MOV     A,M             ;INCREMENT BCD DIGIT
        ADI     1
        MOV     M,A
        JMP     DI0
DI1:
        MOV     A,E             ;ADJUST ACCUMULATOR FOR NEXT SEQUENCE
        ADD     C
        MOV     E,A
        MOV     A,D
        ADC     B
        MOV     D,A
        INX     H               ; HL + -> HL
        RET
;
;
;
;
;
;
;
;
;
;
;
;
;
;
;       ************
;       * LITE.MAC *
;       ************
;
;
        CSEG
LITEON: MVI     A,05H           ;INDEPENDENT BIT SET ROUTINE
        OUT     07H
        RET
LITEOF: MVI     A,04H
        OUT     07H
        RET
IFION:  MVI     A,02H
        OUT     07H
        RET
IFIOFF: MVI     A,03H
        OUT     07H
        RET
SLOINT: XRA     A
        OUT     07H
        RET
FASINT: MVI     A,01H
        OUT     07H
        RET
;
;
;
;
;
;
;
;
;
```

```
;       **********
;       * REQ.MAC *
;       **********
;
REQ:    IN      05H
        ANI     20H
        JNZ     REQ         ;WAIT FOR START
        MOV     B,A         ;FILTER BOUNCE
        PUSH    B
        POP     B
        PUSH    B
        POP     B
        PUSH    B
        POP     B
        IN      05H
        ANI     20H
        CMP     B
        JNZ     REQ
        RET
```

```
;
;
;
;
;
;
;
;
;
;
;
;
;
;
;
;
;
;
;
;
;
;
;
;
;
;
;
;
;
;
;
;
;
;
;                **********
;                * GET.MAC *
;                **********
;
;
GET:    IN      05H
        ANI     10H
        JZ      GET         ;WAIT FOR CONVERSION COMPLETE
        PUSH    B
        POP     B
GET1:   IN      05H
        ANI     10H
        JNZ     GET1
        PUSH    B
        POP     B
        IN      04H
        MOV     M,A
        INX     H
        IN      05H
        ANI     0FH
        MOV     M,A
        RET
        END

C               METFLN.FOR
C               **********

SUBROUTINE FLURO
C       PROGRAM WITHOUT FASTINT
        LOGICAL NUM(32)
        DIMENSION DATA(32),DATN(32),T(32)
```

```
            DIMENSION IDAT(64),NUMBER(32)
            DIMENSION DAT(64),REF(64),ALED(64)
            COMMON/AREA1/IDATA(64)
            COMMON/AREA2/L,DNUM
            COMMON/AREA3/ICAL,ICOPY,IRUN
            CALIB=4
            ICAL=0
            ICOPY=0
            IRUN=0
   10       CALL INIT
            CALL SWITCH
            IF(ICOPY.EQ.1.AND.IRUN.EQ.1) GOTO 722
            DO 20 J=1,64
            IDAT(J)=0
            DAT(J)=0
            REF(J)=0
   20       ALED(J)=0
            CALL DATUM
            DO 30 K=1,15
            CALL DATUM
            DO 35 J=1,64
   35       DAT(J)=DAT(J)+IDATA(J)
   30       CONTINUE
            CALL LITEOF
            DELAY=120
            DO 36 J=1,2200
   36       DELAY=DELAY+1
            DO 40 K=1,15
            CALL DATUM
            DO 45 J=1,64
   45       REF(J)=REF(J)+IDATA(J)
   40       CONTINUE
            CALL LEDON
            DO 65 J=1,1000
            DELAY=DELAY+1
            DO 52 K=1,15
            CALL DATUM
            DO 55 J=1,64
   55       ALED(J)=ALED(J)+IDATA(J)
   52       CONTINUE
            CALL LEDOFF
            CALL LITEON
            DO 60 J=1,64
            DAT(J)=DAT(J)-REF(J)
   60       ALED(J)=ALED(J)-REF(J)
            RCAL=0
            DO 70 J=2,64
   70       RCAL=RCAL+ALED(J)
            RCAL=RCAL/2.0
            DO 75 J=2,63
            K=J-1
   75       DAT(J)=(DAT(K)+DAT(K+1)+DAT(K+2))/3
            DAT(1)=(DAT(1)+DAT(2))/2
            DAT(64)=(DAT(63)+DAT(64))/2
            DO 80 K=1,32
            L=2*K-1
            DATA(K)=DAT(L+1)+DAT(L)
   80       DATA(K)=(CALIB*DATA(K)*.5)/RCAL
            IF(ICAL.EQ.1) GOTO 440
   85       DPOST=0
            DMID=0
```

```
            DANT=0
            DO 81 J=2,11
            K1=J+10
            K2=J+20
            DPOST=DPOST+DATA(J)
            DMID=DMID+DATA(K1)
 81         DANT=DANT+DATA(K2)
            CALL SIGNON
            DPOST=DPOST/10.0
            DMID=DMID/10.0
            DANT=DANT/10.0
            DNUM=DPOST
            CALL EXPSET
            IPOST=100*DNUM
            CALL AVER(3,IPOST,L)
            DNUM=DMID
            CALL EXPSET
            IMID=100*DNUM
            CALL AVER(2,IMID,L)
            DNUM=DANT
            CALL EXPSET
            IANT=100*DNUM
            CALL AVER(1,IANT,L)
 95         DMAX=DATA(23)
            DO 100 J=23,32
            IF(DATA(J).LT.DMAX) GOTO 100
            DMAX=DATA(J)
 100        CONTINUE
 101        IF(DMAX.LT..001) GOTO 620
            DO 110 J=1,32
 110        DATN(J)=DATA(J)/DMAX
            DNUM=DMAX
            CALL EXPSET
            DMAX=DNUM
            IF(DMAX.GT.3.5) GOTO 320
            IF(DMAX.LT.1.4) GOTO 310
            CALL PUTEXP(L)
            CALL PHEAD
            CALL SCALE3
            DO 202 J=1,32
            V=DMAX*DATN(J)*31/3.4
            CALL ROUND(V)
 202        NUMBER(J)=V
            GOTO 415
 320        L=L-1
            CALL PUTEXP(L)
            CALL PHEAD
            CALL SCALE1
            DO 305 J=1,32
            V=DMAX*DATN(J)*31/13.6
            CALL ROUND(V)
 305        NUMBER(J)=V
            GOTO 415
 310        CALL PUTEXP(L)
            CALL PHEAD
            CALL SCALE1
 402        DO 410 J=1,32
            V=DMAX*DATN(J)*31/1.36
            CALL ROUND(V)
 410        NUMBER(J)=V
 415        DO 420 J=1,32
```

```
            IF(NUMBER(J).GT.34) NUMBER(J)=34
            IF(NUMBER(J).LT.1) NUMBER(J)=1
            NUM(J)=NUMBER(J)
420         CONTINUE
            GOTO 430
600         DO 610 J=1,32
610         NUM(J)=1
            CALL PUTEXP(9)
            CALL PHEAD
            CALL SCALE1
430         CALL PLOT(NUM)
C           THE DATA IN NG/ML
440         DO 450 J=1,32
            V=1000*DATA(J)
            CALL ROUND(V)
450         IDATA(J)=V
            CALL HEAD
            CALL PRBLK(IDATA)
            IRUN=1
            ICOPY=0
            ICAL=0
            GOTO 10
700         CALL SIGNON
            DMAX=DATA(1)
            DO 710 J=2,32
            IF(DATA(J).LT.DMAX) GOTO 710
            DMAX=DATA(J)
710         CONTINUE
            GOTO 101
            END
            SUBROUTINE ROUND(V)
            IV=V
            A=V-IV
            IF(A.GT..5) IV=IV+1
            V=IV
            RETURN
            END
            SUBROUTINE DATUM
            COMMON/AREA1/IDATA(64)
            CALL REQ
            DO 10 I=1,64
            CALL GET(J)
10          IDATA(I)=J
            RETURN
            END
            SUBROUTINE EXPSE1
            COMMON/AREA2/L,DNUM
            IF(DNUM.LT..01) GOTO 20
            IF(DNUM.LT..1) GOTO 30
            IF(DNUM.LT.1.0) GOTO 40
            IF(DNUM.LT.10) GOTO 50
            IF(DNUM.LT.100) GOTO 60
            DNUM=DNUM/100.0
            L=5
            GOTO 120
20          DNUM=DNUM/(0.01)
            L=9
            GOTO 100
30          DNUM=DNUM/(0.01)
            L=9
            GOTO 100
```

```
40      DNUM=DNUM/(0.1)
        L=8
        GOTO 100
50      DNUM=DNUM
        L=7
        GOTO 100
60      DNUM=DNUM/10.0
        L=6
100     RETURN
        END
        SUBROUTINE XCALIB
        COMMON/AREA3/ICAL,ICOPY,IRUN
        ICAL=1
        RETURN
        END
        SUBROUTINE XCOPY
        COMMON/AREA3/ICAL,ICOPY,IRUN
        ICOPY=1
        RETURN
        END
```

We claim:

1. An apparatus for determining the concentration of an administered fluorescent material at a plurality of locations in an eye which comprises:
   (a) light source means for exciting the fluorescent material along a path length in the eye to emit fluorescence; and
   (b) means for imaging fluorescence responsive to said excitation simultaneously at a plurality of locations along said path length.

2. The apparatus according to claim 1 wherein said means for imaging further includes optical means for forming an image of the fluorescence along said path length and detection means for detecting substantially simultaneously fluorescence at a plurality of discrete locations along said path length.

3. In a fluorophotometer for measuring the concentration of a fluorescent substance such as fluorescein in the eye of a subject to whom a quantity of such substance was previously administered of the type having a source of light to emit a beam for exciting said fluorescein to allow measurement of fluorescein concentration in the eye, the improvement characterized by:
   (a) stationary optical means for imaging fluorescence simultaneously along a path length within the eye; and
   (b) detecting means for detecting said optically imaged path length and for generating signals representative of fluorescent concentration at a plurality of locations along said imaged path length.

4. Apparatus according to claim 3 wherein said detecting means comprises a linear photodiode array having a plurality of photodiode sensor elements.

5. The apparatus according to claim 4 wherein said detecting means further comprises:
   (a) means for scanning said linear photodiode array and for generating analog signals representing the fluorescent concentration detected by each of said sensor elements;
   (b) means for converting the analog signals to digital data; and
   (c) microprocessor means for generating information identifying the concentration of the fluorescent substance in response to the digital data.

6. In a fluorophotometer for determining the concentration of fluorescence in an eye of the type where the fluorescence is excited with a beam of light adapted to enter and transverse a path in the eye, the beam of light being produced by a source of light the improvement comprising:
   (a) a self-contained head being connectable to the source of light, said head including
      (i) stationary optical means for imaging simultaneously fluorescence emitted along the entire path at a detecting plane,
      (ii) a linear photodiode array, positioned at the detecting plane, for detecting the fluorescence emitted along the path and for generating analog signals representing the detected fluorescence,
      (iii) an analog-to-digital converter connected to said linear photodiode array, said converter converting the analog signals to digital data and generating a status signal at the end of each conversion, said linear photodiode array being reset in response to the status signal, and
      (iv) means for clocking said linear photodiode array to start the scanning and for clocking said converter to start the conversion; and
   (b) programmable microprocessor means, coupled to said self-contained head, for generating information identifying the concentration of the fluorescence in response to the digital data.

* * * * *